(12) United States Patent
Lee

(10) Patent No.: US 9,354,150 B2
(45) Date of Patent: May 31, 2016

(54) TEST APPARATUS FOR A FLEXIBLE DEVICE

(71) Applicant: SAMSUNG DISPLAY CO., LTD., Yongin, Gyeonggi-Do (KR)

(72) Inventor: Sang Wol Lee, Yongin-si (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 334 days.

(21) Appl. No.: 14/153,243

(22) Filed: Jan. 13, 2014

(65) Prior Publication Data

US 2015/0033870 A1    Feb. 5, 2015

(30) Foreign Application Priority Data

Aug. 2, 2013    (KR) .................. 10-2013-0092198

(51) Int. Cl.
*G01N 3/20* (2006.01)
(52) U.S. Cl.
CPC .......... *G01N 3/20* (2013.01); *G01N 2203/0278* (2013.01); *G01N 2203/0282* (2013.01)
(58) Field of Classification Search
CPC .................... G01N 3/20; G01N 2203/0023
USPC ........................................... 73/849
See application file for complete search history.

(56) References Cited

U.S. PATENT DOCUMENTS

| 2012/0067134 A1* | 3/2012 | Bell | G02F 1/133305 73/800 |
| 2014/0333333 A1* | 11/2014 | Seol | G01R 31/2874 324/750.03 |

FOREIGN PATENT DOCUMENTS

| JP | 2005-030863 | 2/2005 | |
| JP | 2007-103843 | 4/2007 | |
| JP | 2012-098141 | 5/2012 | |
| KR | 1020090115370 | 11/2009 | |
| KR | 1020100016826 | 2/2010 | |
| KR | 1020110114256 | 10/2011 | |
| KR | 1020120013056 | 2/2012 | |
| KR | 1020120127037 | 11/2012 | |
| KR | WO 2015064819 A1 * | 5/2015 | ............... G01N 3/20 |

* cited by examiner

*Primary Examiner* — Lisa Caputo
*Assistant Examiner* — Jamel Williams
(74) *Attorney, Agent, or Firm* — F. Chau & Associates, LLC

(57) ABSTRACT

A test apparatus for a flexible device includes a rotational driving unit, a first support, and a second support. The rotational driving unit is configured to generate a rotational force. The first support is coupled to the rotational driving unit, and is configured to rotate in response to the rotational force and support a first portion of the flexible device. The second support is disposed adjacent to the first support and is configured to support a second portion of the flexible device.

20 Claims, 11 Drawing Sheets

TEST APPARATUS FOR A FLEXIBLE DEVICE

CROSS-REFERENCE TO RELATED APPLICATIONS

This application claims priority under 35 U.S.C. §119 to Korean Patent Application No. 10-2013-0092198, filed on Aug. 2, 2013, the disclosure of which is hereby incorporated by reference in its entirety.

TECHNICAL FIELD

Exemplary embodiments of the present inventive concept relate to a test apparatus for a flexible device, and more particularly, to a test apparatus configured to test flexible characteristics of a flexible device.

DISCUSSION OF THE RELATED ART

The use of flexible displays in electronic devices is increasing. A flexible display has flexible characteristics, allowing the display to be bent, which can improve portability and storage.

A test process for testing the flexible characteristics of a flexible device such as, for example, flexible displays, flexible display panels, flexible substrates, base substrates of flexible substrates, etc., may be performed to determine the reliability of the flexible device, since an unreliable flexible device may be damaged as a result of bending the flexible device.

SUMMARY

Exemplary embodiments of the present inventive concept provide a test apparatus that is capable of testing flexible characteristics of a flexible device.

According to an exemplary embodiment of the present inventive concept, a test apparatus for a flexible device includes a rotational driving unit, a first support, and a second support. The rotational driving unit generates rotational force. The first support is coupled to the rotational driving unit, rotates in response to the rotational force, and supports a first portion of the flexible device. The second support is disposed adjacent to the first support and supports a second portion of the flexible device.

According to an exemplary embodiment of the present inventive concept, a test apparatus for a flexible device includes a rotational driving unit, a first rotational moving unit, and a second rotational moving unit. The rotational driving unit generates rotational force. The first rotational moving unit supports a first portion of the flexible device, is coupled to the rotational driving unit, and rotates in response to the rotational force. The second rotational moving unit supports a second portion of the flexible device and rotates in a direction opposite to the rotation direction of the first rotational moving unit.

According to an exemplary embodiment of the present inventive concept, a test apparatus for a flexible device includes a rotational driving unit and a first linear moving unit. The rotational driving unit generates rotational force. The first linear moving unit is coupled to the rotational driving unit and converts the rotational force into a linear motion. The first linear moving unit is coupled to a first portion of the flexible device and stretches the first portion of the flexible device.

BRIEF DESCRIPTION OF THE DRAWINGS

The above and other features of the present inventive concept will become more apparent by describing in detail exemplary embodiments thereof with reference to the accompanying drawings, in which.

DETAILED DESCRIPTION OF THE EXEMPLARY EMBODIMENTS

Figure 1:
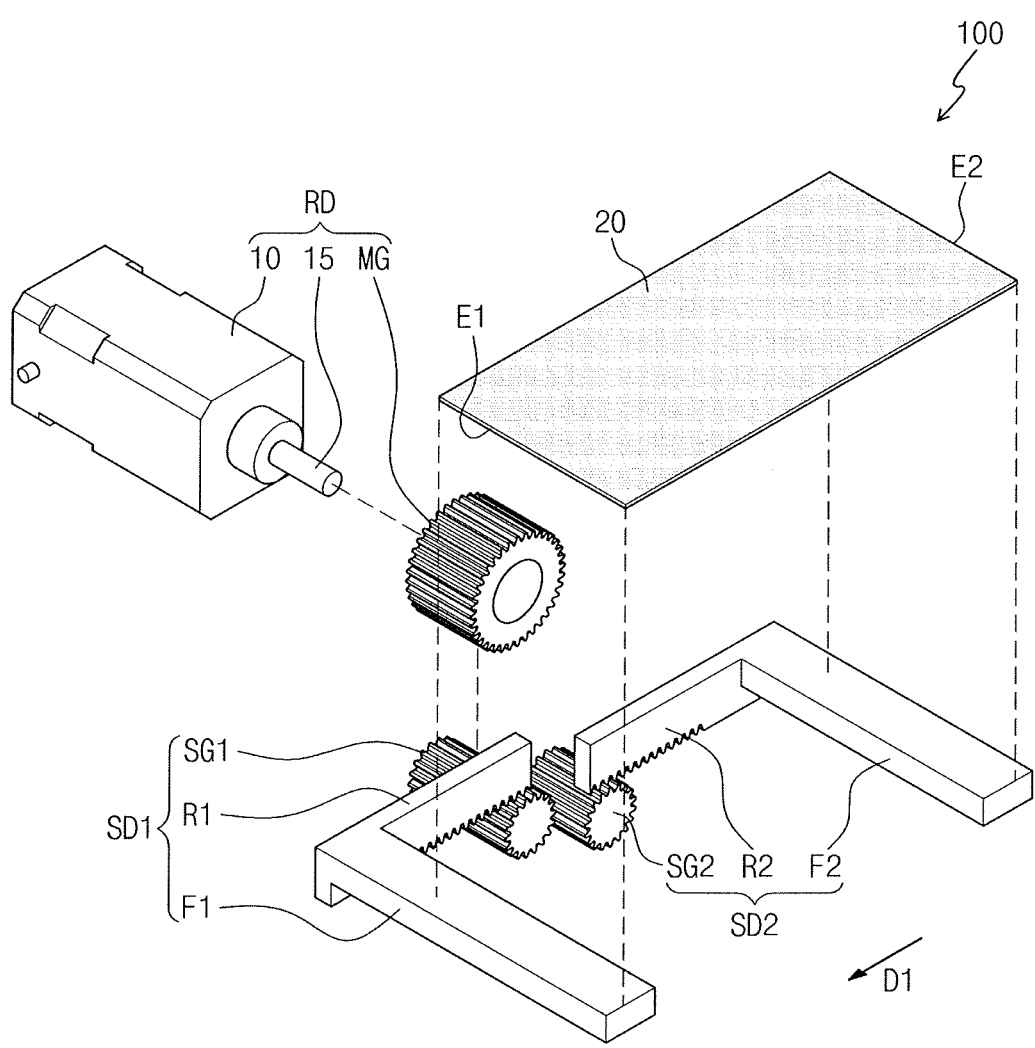
FIG. 1 is a perspective view illustrating a test apparatus for a flexible device, according to an exemplary embodiment of the present inventive concept.

Exemplary embodiments of the present inventive concept will be described more fully hereinafter with reference to the accompanying drawings. Like reference numerals may refer to like elements throughout the accompanying drawings.

It will be understood that although the terms 'first' and 'second' may be used herein to describe various components, these components should not be limited by these terms. It will be further understood that when a component is referred to as being 'on', 'connected to', 'coupled to', or 'adjacent to' another component, it can be directly on, connected to, coupled to, or adjacent to the other component, or intervening components may also be present. It will also be understood that when a component is referred to as being 'between' two components, it can be the only component between the two components, or one or more intervening components may also be present.

FIG. 1 is a perspective view illustrating a test apparatus for a flexible device, according to an exemplary embodiment of the present inventive concept.

Referring to FIG. 1, a test apparatus 100 is configured to test a stretch rate of the flexible device 20. The stretch rate of the flexible device 20 may refer to the amount of stretching the flexible device 20 may withstand without incurring damage. In exemplary embodiments, the test apparatus 100 may stretch the flexible device 20 in multiple different directions to test the physical characteristics such as, for example, the tensile strength, of the flexible device 20.

The flexible device 20 to be tested by the test apparatus 100 may be, for example, a flexible display panel including two flexible substrates that are coupled to face each other. However, exemplary embodiments of the present inventive concept are not limited thereto. For example, the flexible device 20 may also be a flexible display device including the flexible display panel and a driving unit for driving the flexible display panel, one of the two flexible substrates described above, or a base substrate including one of the two flexible substrates described above.

In the exemplary embodiment of FIG. 1, the test apparatus 100 includes a rotational driving unit RD, a first linear moving unit SD1, and a second linear moving unit SD2.

The rotational driving unit RD includes a motor 10 and a main gear MG. The motor 10 includes a rotation shaft 15. The motor 10 receives power from an external source and generates a rotational force, which is transferred to the rotation shaft 15.

The main gear MG is coupled to the rotation shaft 15. The main gear MG rotates in the same direction as the rotation shaft 15 as a result of the rotational force. In the exemplary embodiment of FIG. 1, the rotation shaft 15 may be inserted into a through hole defined in the main gear MG and coupled to the main gear MG. In this case, the main gear MG may be fixed to the rotation shaft 15 using, for example, a screw that passes through the main gear MG and is coupled to the rotation shaft 15.

The first linear moving unit SD1 is coupled to a first portion E1 of the flexible device 20, and to the rotational driving unit RD, which results in the conversion of the rotational force into a linear motion. As a result, the first linear moving unit SD1 may stretch the first portion E1 in a direction (e.g., a first direction D1) in which the first linear moving unit SD1 linearly moves. The first linear moving unit SD1 will be described in further detail with reference to FIGS. 2A and 2B.

The first linear moving unit SD1 includes a first sub gear SG1, a first rack R1, and a first support F1.

The first sub gear SG1 is coupled to the main gear MG and rotates in a direction opposite to the direction in which the main gear MG rotates. The first sub gear SG1 may be disposed under the main gear MG, as shown in FIG. 1. The main gear MG and the first sub gear SG1 each include a plurality of teeth, and each of the teeth of the first sub gear SG1 may have the same pitch, or substantially the same pitch, as the pitch of each of the teeth of the main gear MG.

Each of the main gear MG and the first sub gear SG1 may be, for example, a spur gear. However, the main gear MG and the first sub gear SG1 are not limited thereto. For example, in an exemplary embodiment, each of the main gear MG and the first sub gear SG1 may be a helical gear.

The main gear MG may have a diameter that is greater than a diameter of the first sub gear SG1. As a result, the main gear MG may have a larger number of teeth than the first sub gear SG1. However, the diameter and number of teeth of the main gear MG and the first sub gear SG1 are not limited thereto. For example, each of the main gear MG and the first sub gear SG1 may be defined in diameter and number of teeth according to a linear moving distance of the first linear moving unit SD1.

The first rack R1 extends in the first direction D1. The first rack R1 is coupled to the first sub gear SG1 and linearly moves in the first direction D1 or a direction opposite to the first direction D1 as the first sub gear SG1 rotates. The first rack R1 may be a type of gear having an infinite pitch diameter. The first rack R1 has teeth that engage the teeth of the first sub gear SG1. Thus, the first rack R1 and the first sub gear SG1 may be coupled to each other in a manner in which a general rack and a general pinion are coupled to each other to convert a rotational motion to a linear motion.

When a side of the flexible device 20 parallel to an expansion direction thereof is defined in length, a linearly moving distance of the first rack R1 may correspond to about 1% to about 50% of the length of the side. Thus, the flexible device 20 may be stretched by a length corresponding to about 1% to about 50% of the length of the side by the first rack R1. However, exemplary embodiments of the present inventive concept are not limited to the linearly moving distance of the first rack R1. That is, the linearly moving distance of the first linear moving unit SD1 may be variable according to the flexible device 20 being tested.

The first support F1 is coupled to the first rack R1. The first support F1 may extend in a direction perpendicular to the first direction D1, and may have a shape that is integrated with the first rack R1. The first support F1 may be coupled to the first portion E1 of the flexible device 20. The first portion E1 may be fixed to the first support F1 using, for example, double-sided tape disposed between the first portion E1 and the first support F1, however, the manner of fixing the first portion E1 to the first support F1 is not limited thereto.

The second linear moving unit SD2 is coupled to a second portion E2 of the flexible device 20. The second linear moving unit SD2 converts the rotational force generated from the rotational driving unit RD into a linear motion. Thus, the second linear moving unit SD2 may be moved in a direction opposite to the direction of the first linear moving unit SD1 (e.g., opposite to the first direction D1). As a result, the second portion E2 of the flexible device 20 may be stretched in the linearly moving direction of the second linear moving unit SD2 by the second linear moving unit SD2.

The second linear moving unit SD2 includes a second sub gear SG2, a second rack R2, and a second support F2.

In the exemplary embodiment of FIG. 1, the second sub gear SG2 is coupled to the first sub gear SG1 and rotates in a direction opposite to the rotation direction of the first sub gear SG1. The second sub gear SG2 rotates in the same direction as the main gear MG. The second sub gear SG2 may be disposed on a side of the first sub gear SG1. The second sub gear SG2 includes a plurality of teeth, and each of the teeth of the second sub gear SG2 may have the same pitch, or substantially the same pitch, as each of the teeth of the main gear MG and the first sub gear SG1. Further, the second sub gear SG2 may have the same diameter as the first sub gear SG1, and the number of teeth of the second sub gear SG2 may be equal to the number of teeth of the first sub gear SG1.

The second rack R2 may extend in the first direction D1. The second rack R2 is coupled to the second sub gear SG2 and linearly moves as the second sub gear SG2 rotates. Similar to the coupling method between the first rack R1 and the first sub gear SG1, the second rack R2 may be coupled to the second sub gear SG2 in the manner in which the general rack and the general pinion are coupled to each other to convert rotational motion to linear motion.

A linearly moving distance of the second rack R2 may be equal to the linearly moving distance of the first rack R1. Thus, as described above, when the linearly moving distance of the first rack R1 corresponds to about 1% to about 50% of the length of the side of the flexible device 20, the linearly moving distance of the second rack R2 may correspond to about 1% to about 50% of the length of the side. Thus, the flexible device 20 may be stretched by a length corresponding to about 1% to about 50% thereof by the second rack R2. As a result, since the first and second racks R1 and R2 stretch the flexible device 20 in directions different from each other (e.g., in opposite directions), the flexible device 20 may be stretched by a length corresponding to about 1% to about 50% thereof by the first and second racks R1 and R2.

The second support F2 is coupled to the second rack R2. The second support F2 may extend in a direction perpendicular to the first direction D1. The second support F2 may be disposed parallel to the first support F1, and may have a shape that is integrated with the second rack R2. The second support F2 may be coupled to the second portion E2 of the flexible device 20. For example, the second portion E2 of the flexible device 20 may be fixed to the second support F2 using double-sided tape disposed between the second portion E2 and the second support F2, however, the manner of fixing the second portion E2 of the flexible device 20 to the second support F2 is not limited thereto.

Hereinafter, an operation for testing the flexible device 20 using the test apparatus 100 will be described with reference to FIGS. 2A and 2B.

Figure 2A:
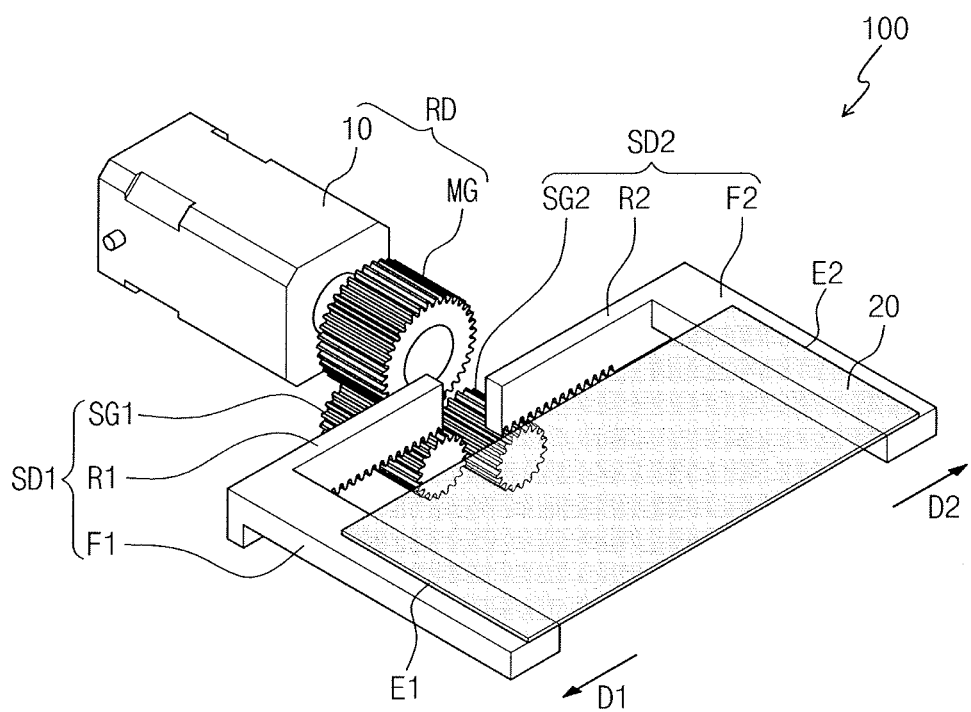
FIGS. 2A and 2B are views illustrating an operation for testing the flexible device using the test apparatus of FIG. 1, according to an exemplary embodiment of the present inventive concept.
Figure 2A:
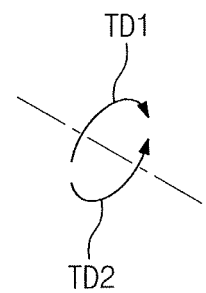
Figure 2B:
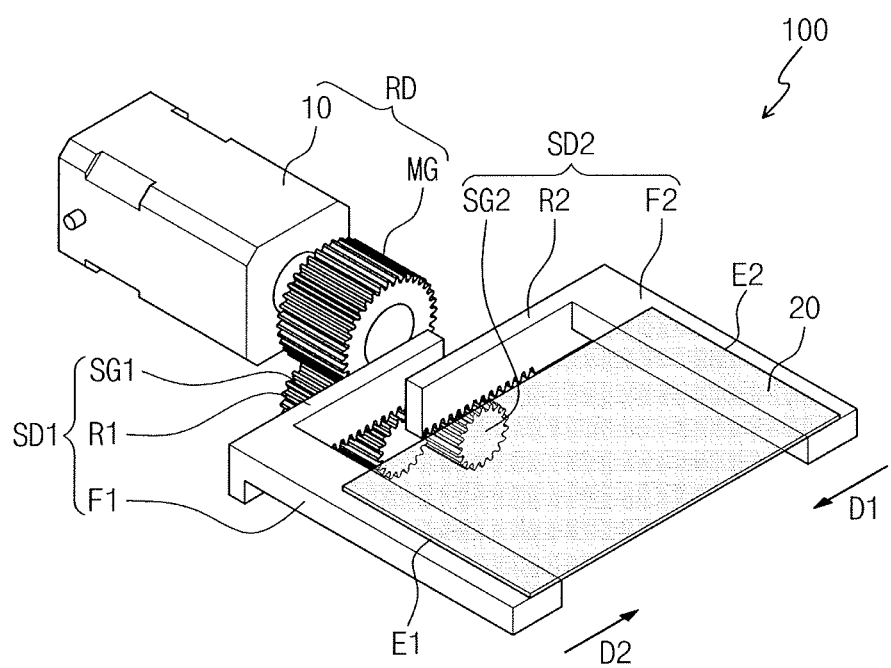
Figure 2B:
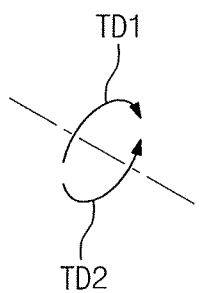

FIGS. 2A and 2B are views illustrating an operation for testing the flexible device using the test apparatus of FIG. 1, according to an exemplary embodiment of the present inventive concept.

Referring to FIG. 2A, the flexible device 20 is disposed on the first and second supports F1 and F2. The first portion E1 of the flexible device 20 is then fixed to the first support F1 using, for example, double-sided tape, and the second portion E2 of the flexible device 20 is fixed to the second support F2 using, for example, double-sided tape.

Thereafter, the motor 10 is driven to allow the rotation shaft 15 (see FIG. 1) to rotate in a first rotation direction TD1. Thus, the main gear MG coupled to the rotation shaft 15 may also rotate in the first rotation direction TD1. In this case, the first sub gear SG1 coupled to the main gear MG rotates in a second rotation direction TD2 opposite to the first rotation direction TD1. As a result, the first rack R1 coupled to the first sub gear SG1 linearly moves in the first direction D1.

In addition, since the second sub gear SG2 rotates in a direction opposite to that of the first sub gear SG1, the second sub gear SG2 rotates in the first rotation direction TD1. As a result, the second rack R2 coupled to the second sub gear SG2 linearly moves in a second direction D2 opposite to the first direction D1.

As described above, when the first and second racks R1 and R2 convert the rotational motion of the first and second sub gears SG1 and SG2 into linear motion, and linearly move in directions different from each other (e.g., opposite directions), the flexible device 20 fixed to the first and second supports F1 and F2 may be stretched in the first and second directions D1 and D2. Further, as described with reference to FIG. 1, since the linearly moving distance of each of the first and second racks R1 and R2 corresponds to about 1% to about 50% of the length of the side of the flexible device 20, the flexible device 20 may be stretched by a length corresponding to about 2% to about 100% thereof by the test apparatus 100.

Referring to FIG. 2B, after the test operation described with reference to FIG. 2A is finished, the motor 10 is driven to allow the main gear MG to rotate in the second rotation direction TD2. As a result, the first sub gear SG1 rotates in the first rotation direction TD1, and the first rack R1 linearly moves in the second direction D2. In addition, the second sub gear SG2 rotates in the second rotation direction TD2, and the second rack R2 linearly moves in the first direction D1.

According to the operation of the test apparatus 100 of FIGS. 2A and 2B, a tension test with respect to the flexible device 20 may be performed by controlling the rotation direction of the rotational force generated from the rotational driving unit RD, and the tensile force applied to the flexible device 20 may be released.

Figure 3:
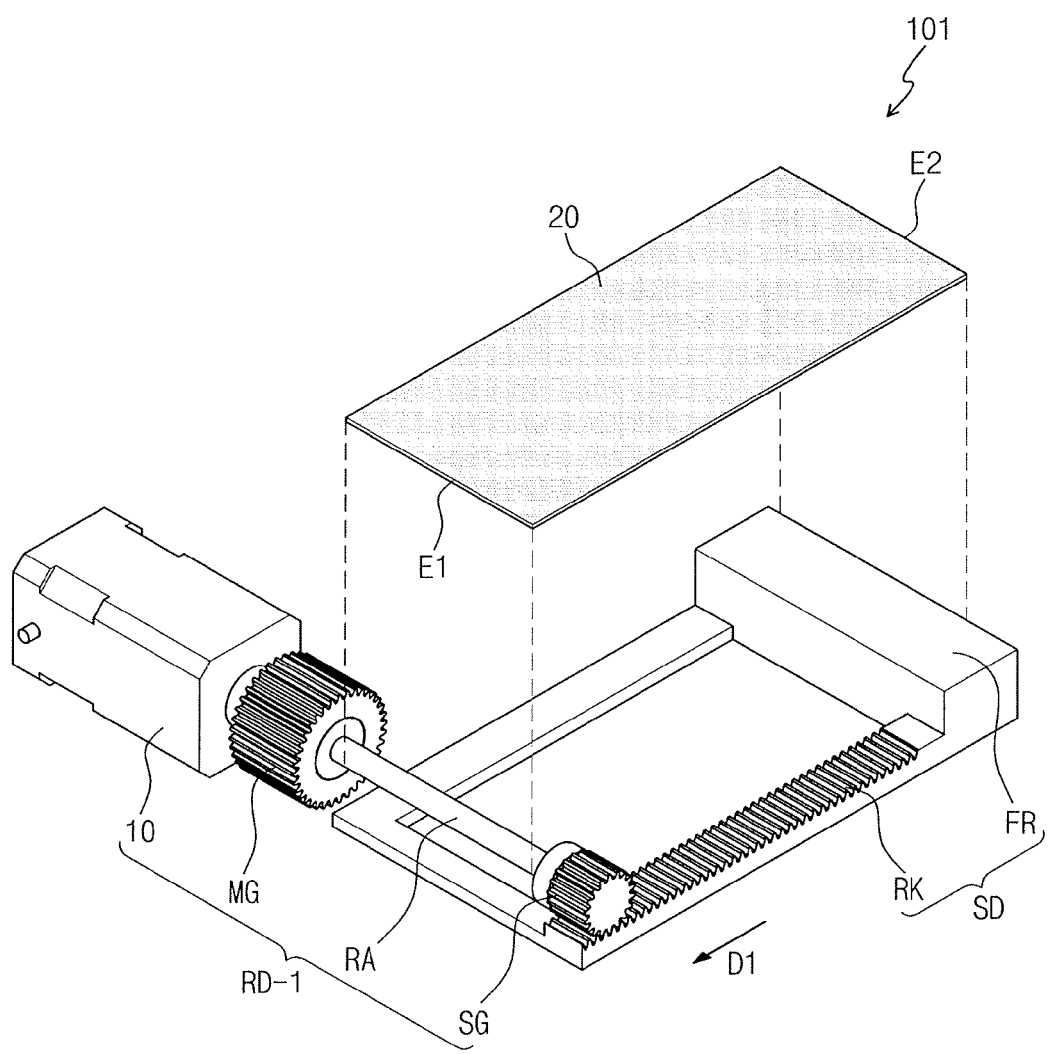
FIG. 3 is a perspective view illustrating a test apparatus for a flexible device, according to an exemplary embodiment of the present inventive concept.

FIG. 3 is a perspective view illustrating a test apparatus for a flexible device, according to an exemplary embodiment of the present inventive concept. In the description of FIG. 3, components previously described with reference to FIG. 1 may be denoted by the same reference numerals used with reference to FIG. 1, and further description of these components may be omitted.

Referring to FIG. 3, a test apparatus 101 according to an exemplary embodiment may be an apparatus for testing a roll rate of a flexible device 20. The role rate of a flexible device may refer to the amount of rolling the flexible device may withstand without incurring damage. The test apparatus 101 includes a rotational driving unit RD-1 and a linear moving unit SD.

The rotational driving unit RD-1 includes a motor 10, a main gear MG, a driving shaft RA, and a sub gear SG. The rotation shaft 15 (see FIG. 1) and the driving shaft RA of the motor 10 may be inserted into a through hole of the main gear MG and coupled to the main gear MG. In this case, the main gear MG may be fixed to each of the rotation shaft 15 and the driving shaft RA using, for example, a screw that passes through the main gear MG and is coupled to the rotation shaft 15 and the driving shaft RA.

Unlike the exemplary embodiment described with reference to FIG. 1, in the exemplary embodiment of FIG. 3, the main gear MG may not be used for transferring rotational force to other sub gears. Rather, the main gear MG may be used for connecting the driving shaft RA to the rotation shaft 15. Thus, the rotational driving unit RD-1 may include a coupling member having, for example, a cylindrical shape, which connects the rotation shaft 15 to the driving shaft RA instead of the main gear MG.

As described above, when the driving shaft RA is coupled to the rotation shaft 15 of the motor 10, the driving shaft RA rotates in the same direction as the rotation shaft 15. Further, the driving shaft RA is coupled to a first portion E1 of the flexible device 20. The first portion E1 of the flexible device 20 may be fixed to the driving shaft RA using, for example, double-sided tape disposed between the driving shaft RA and the first portion E1.

As described above, an end of the driving shaft RA may be coupled to the rotation shaft 15 of the motor 10 by the main gear MG, and the other end of the driving shaft RA may be coupled to the sub gear SG. The driving shaft RA may be fixed to the sub gear SG using, for example, a screw that passes through the sub gear SG and is coupled to the driving shaft RA. Thus, the sub gear SG may rotate in the same direction as the driving shaft RA.

The linear moving unit SD includes a rack RK and a support FR. The rack RK has a shape extending in a first direction D1, and the rack RK may be coupled to the sub gear SG and linearly moves as the sub gear SG rotates. The rack RK and the sub gear SG may be coupled to each other in the manner in which the general rack and the general pinion are coupled to each other to convert rotational motion into linear motion, similar to the coupling manner between the first sub gear SG1 (see FIG. 1) and the first rack R1 (see FIG. 1), as shown in FIG. 1.

The support FR extends in a direction perpendicular to the first direction D1 and is coupled to the rack RK. The support FR may be disposed parallel to the driving shaft RA. The support FR may have a frame shape that is integrated with the rack RK. Further, the support FR may be coupled to a second portion E2 of the flexible device 20. The second portion E2 of the flexible device 20 may be fixed to the support FR using, for example, double-sided tape disposed between the second portion E2 and the support FR, however, the manner of fixing the second portion E2 to the support FR is not limited thereto.

Hereinafter, an operation for testing the flexible device 20 using the test apparatus 101 will be described with reference to FIGS. 4A and 4B, according to an exemplary embodiment of the present inventive concept.

Figure 4A:
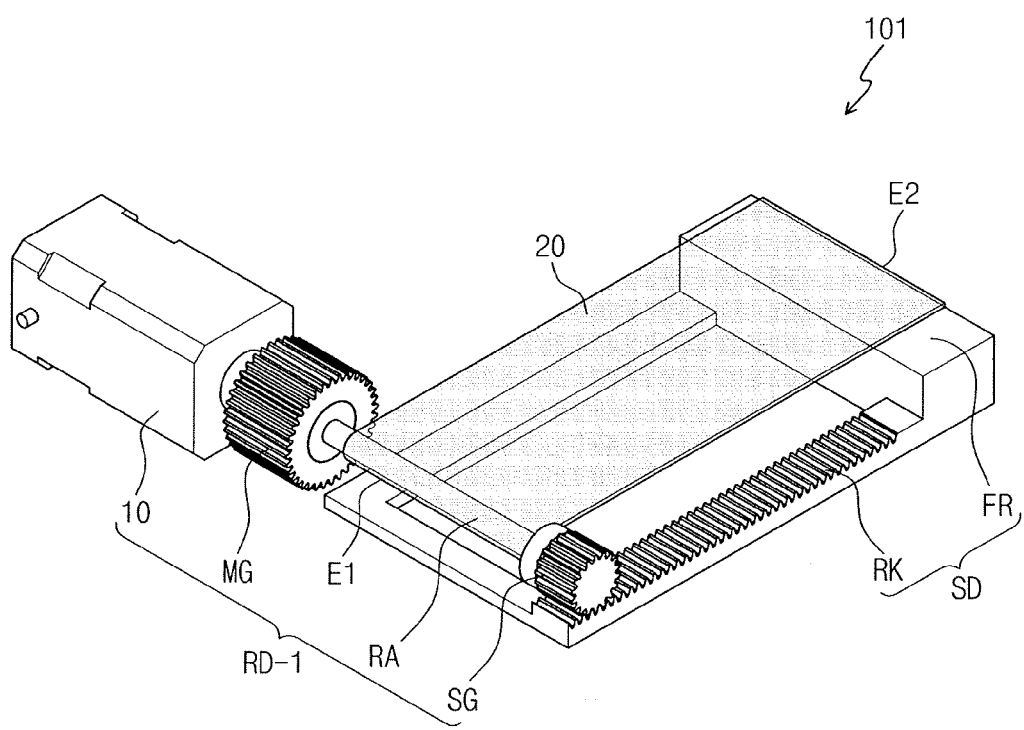
FIGS. 4A and 4B are views illustrating an operation for testing the flexible device using the test apparatus of FIG. 3, according to an exemplary embodiment of the present inventive concept.
Figure 4B:
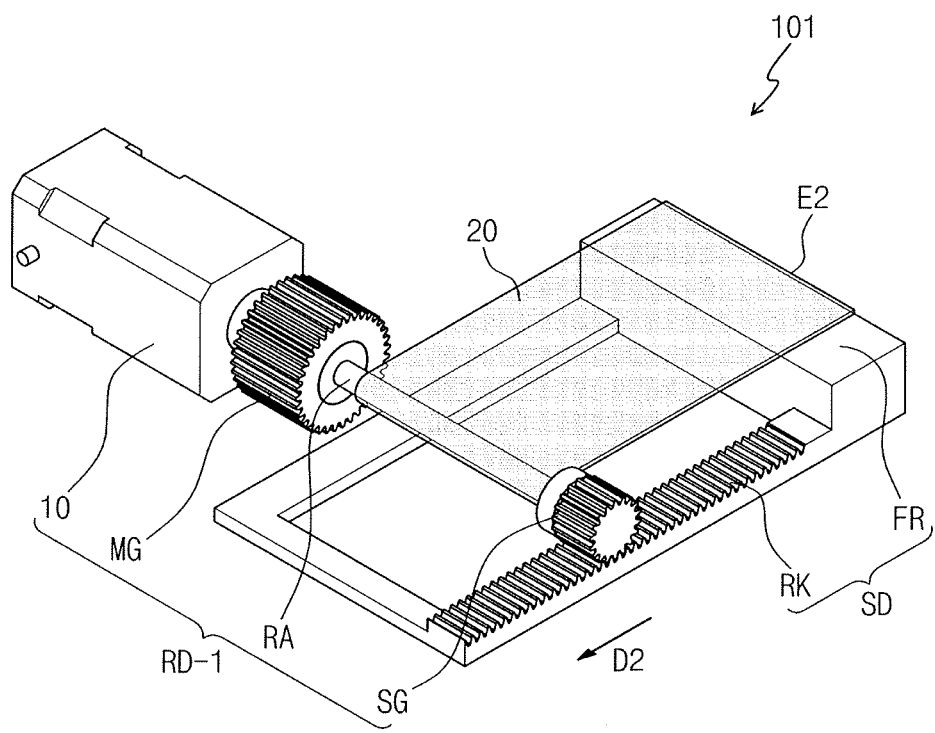
Figure 4B:
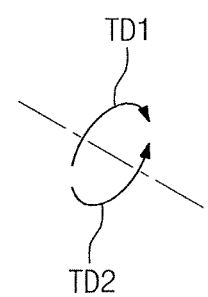

FIGS. 4A and 4B are views illustrating an operation for testing the flexible device using the test apparatus 101 of FIG. 3, according to an exemplary embodiment of the present inventive concept.

Referring to FIGS. 4A and 4B, the first portion E1 of the flexible device 20 is fixed to the driving shaft RA, and the second portion E2 of the flexible device 20 is fixed to the support FR. The motor 10 is then driven to allow the rotation shaft 15 (see FIG. 1) to rotate in a first rotation direction TD1. As a result, the driving shaft RA rotates in the first rotation direction TD1 and winds the first portion E1 of the flexible device 20 fixed to the driving shaft RA around the driving shaft RA.

The sub gear SG coupled to the driving shaft RA is rotated in the first rotation direction TD1. Thus, the rack RK coupled to the sub gear SG linearly moves in a second direction D2. As a result, the support FR coupled to the rack RK linearly moves together with the rack RK in the second direction D2.

Since the rack RK linearly moves when the first portion E1 of the flexible device 20 is being wound around the driving shaft RA, the support FR linearly moves to approach the driving shaft RA. As a result, since the flexible device 20 is rolled around the driving shaft RA while the driving shaft RA rotates, a roll rate of the flexible device 20 may be tested by the test apparatus 101.

Figure 5A:
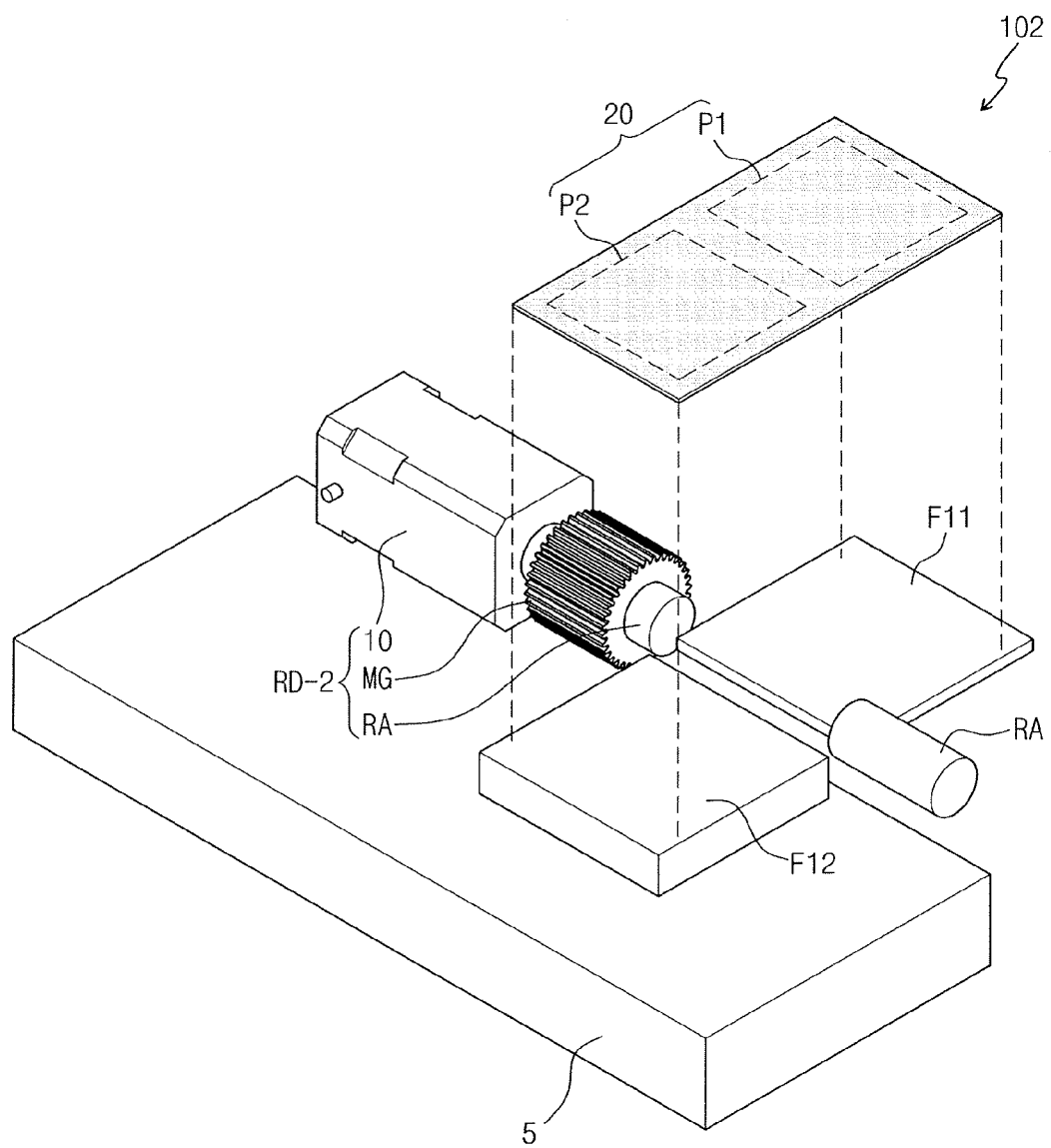
FIG. 5A is a perspective view illustrating a test apparatus for a flexible device, according to an exemplary embodiment of the present inventive concept.
Figure 5B:
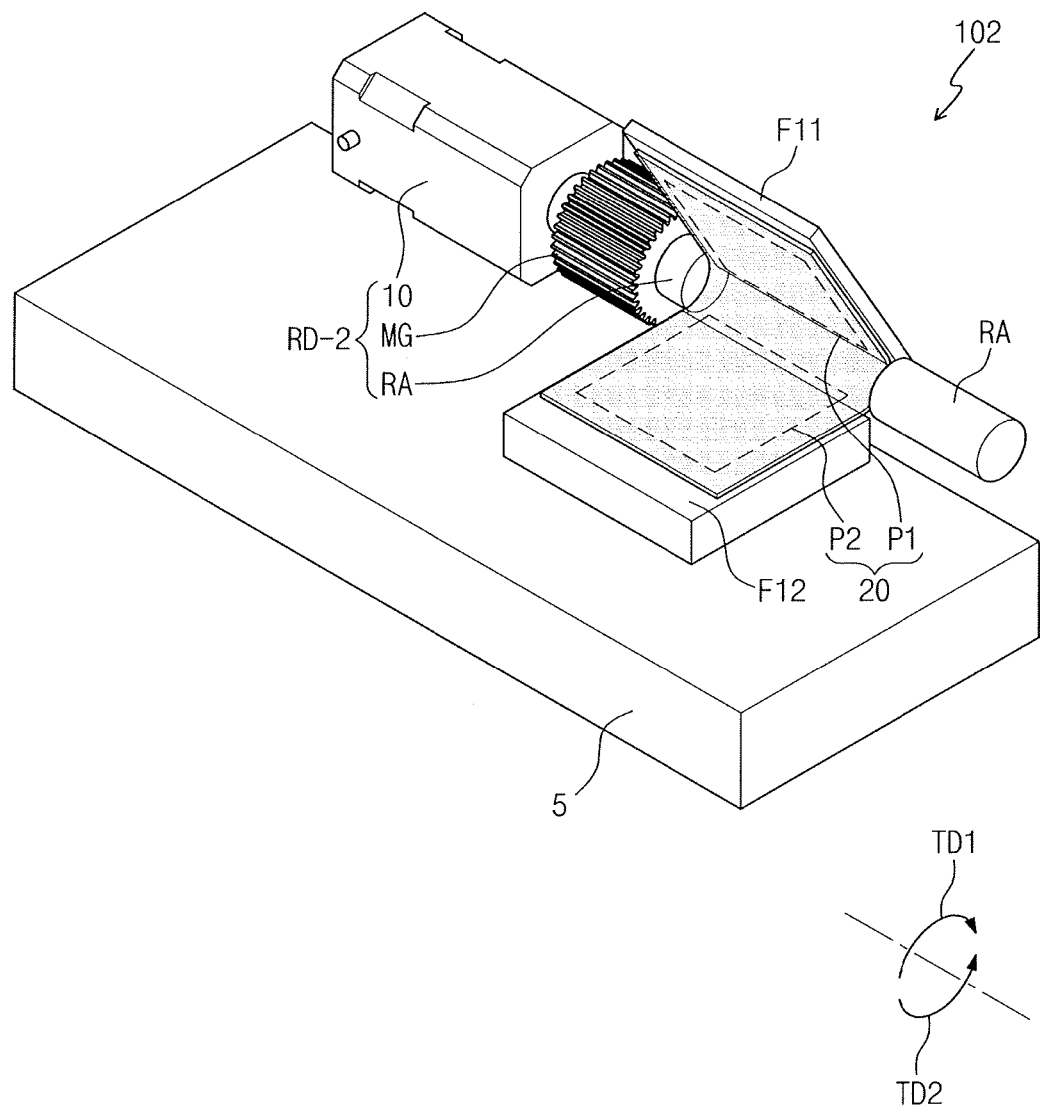
FIG. 5B is a view illustrating an operation for testing the flexible device using the test apparatus of FIG. 5A, according to an exemplary embodiment of the present inventive concept.

FIG. 5A is a perspective view illustrating a test apparatus for a flexible device, according to an exemplary embodiment of the present inventive concept. FIG. 5B is a view illustrating an operation for testing the flexible device using the test apparatus of FIG. 5A. In the description of FIGS. 5A and 5B, components previously described may be denoted by the same reference numerals previously used, and further description of these components may be omitted.

Referring to FIGS. 5A and 5B, a test apparatus 102 according to an exemplary embodiment may be an apparatus for testing a fold rate of a flexible device 20. The fold rate of the flexible device 20 may refer to the amount of folding the flexible device 20 may withstand without incurring damage. The test apparatus 102 includes a support member 5, a first support F11, a second support F12, and a rotational driving unit RD-2.

The rotational driving unit RD-2 includes a motor 10, a main gear MG, and a driving shaft RA. Similar to the exemplary embodiment described with reference to FIG. 3, the main gear MG may not be used for transferring rotational force to other sub gears. Rather, the main gear MG may be used for connecting the driving shaft RA to the rotation shaft 15 of the motor 10. Thus, the rotational driving unit RD-2 may include a coupling member having, for example, a cylindrical shape, which connects the rotation shaft 15 to the driving shaft RA instead of the main gear MG.

The first support F11 is fixed to the driving shaft RA. Thus, the first support F11 rotates as the driving shaft RA rotates. Further, the first support F11 may support a first portion P1 of the flexible device 20. In this case, double-sided tape may be provided between the first portion P1 and the first support F11 to fix the first portion P1 to the first support F11, however, the fixing means are not limited thereto.

The second support F12 is disposed on the support member 5 and fixed to the support member 5. The second support F12 is disposed parallel and adjacent to the first support F11. The second support F12 may support a second portion P2 of the flexible device 20. In this case, double-sided tape may be provided between the second portion P2 and the second support F12 to fix the second portion P2 to the second support F12, however, the fixing means are not limited thereto.

Referring to FIG. 5B, when power is supplied to the motor 10 to allow the rotation shaft 15 of the motor 10 to rotate in a second rotation direction TD2, the driving shaft RA, together with the rotation shaft 15, rotates in the second rotation direction TD2. As a result, the first support F11 fixed to the driving shaft RA rotates in the second rotation direction TD2 using the driving shaft RA as a rotation shaft (e.g., the first support F11 rotates about an axis defined by the driving shaft RA). Thus, the first portion P1 disposed on the first support F11 rotates together with the first support F11 in the second rotation direction TD2 using the driving shaft RA as a rotation shaft (e.g., the first portion P1 disposed on the first support F11 rotates together with the first support F11 about an axis defined by the driving shaft RA).

Since the second support F12 is fixed to the support member 5 while the first support F11 and the first portion P1 rotate, the second portion P2 is also fixed, and the flexible device 20 is folded. As a result, a fold rate of the flexible device 20 with respect to the test apparatus 102 may be tested.

In addition, the first support F11 may rotate in a first rotation direction TD1 or the second rotation direction TD2 by controlling the rotation direction of the rotation shaft 15 of the motor 10. Thus, the test apparatus 102 may test the fold rate of the flexible device 20. When folded, the first and second portions P1 and P2 of the flexible device 20 may have an angle of about 0° to about 270° therebetween.

Figure 6:
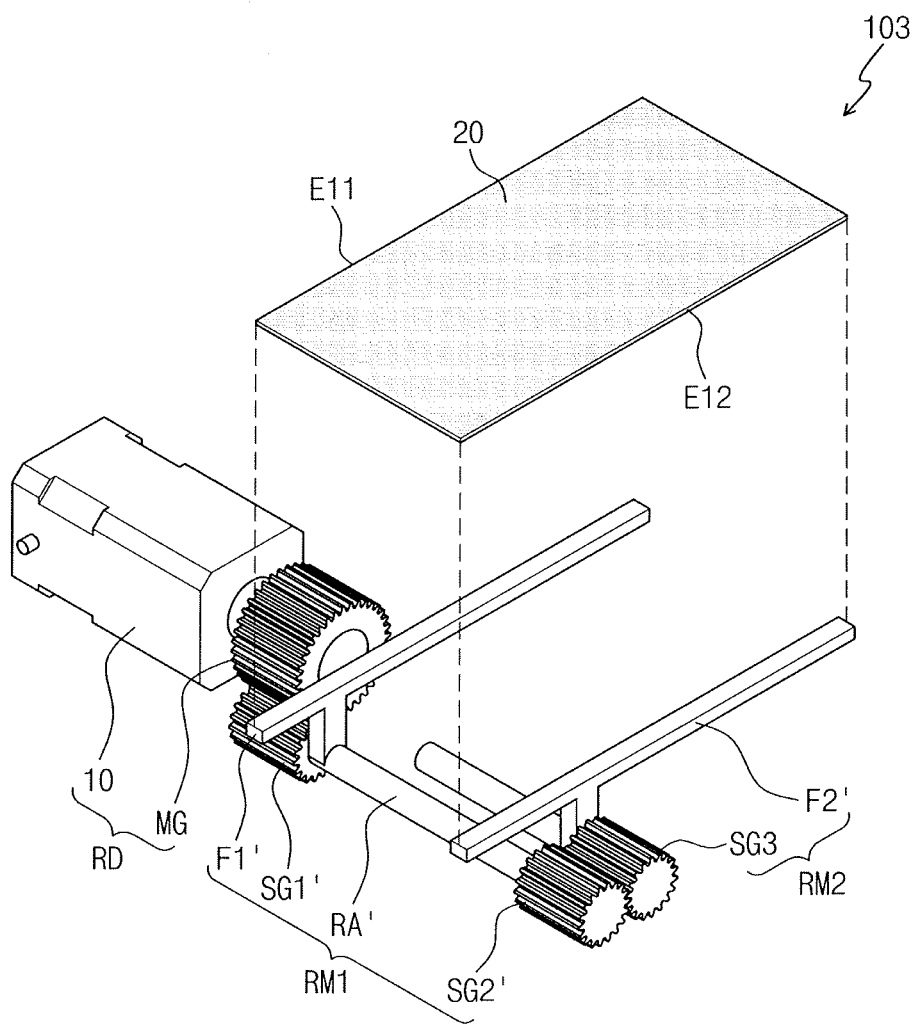
FIG. 6 is a perspective view illustrating a test apparatus for a flexible device, according to an exemplary embodiment of the present inventive concept.

FIG. 6 is a perspective view illustrating a test apparatus for a flexible device, according to an exemplary embodiment of the present inventive concept. In the description of FIG. 6, components previously described may be denoted by the same reference numerals previously used, and further description of these components may be omitted.

Referring to FIG. 6, a test apparatus 103 according to an exemplary embodiment may be an apparatus for testing a twist rate of a flexible device 20. The twist rate of the flexible device 20 may refer to the amount of twisting the flexible device 20 may withstand without incurring damage. The test apparatus 103 includes a rotational driving unit RD, a first rotational moving unit RM1, and a second rotational moving unit RM2.

The first rotational moving unit RM1 generates rotational force using a motor 10. The rotational force may be transferred to a rotation shaft 15 (see FIG. 1) of the motor 10 and a main gear MG coupled to the rotation shaft 15.

The first rotational moving unit RM1 supports a first portion E11 of the flexible device 20, and the first rotational moving unit RM1 is coupled to the rotational driving unit RD such that it is rotated as a result of the rotational force. The first rotational moving unit RM1 includes a first sub gear SG1', a first support F1', a driving shaft RA', and a second sub gear SG2'.

The first sub gear SG1' is coupled to the main gear MG and rotates in a direction opposite to the direction in which the main gear MG rotates. The first support F1' is fixed to the first sub gear SG1', and the first portion E11 of the flexible device 20 is fixed to the first support F1'.

The driving shaft RA' includes an end coupled to the first sub gear SG1'. As a result, the driving shaft RA' rotates in the same direction as the rotation direction of the first sub gear SG1'. Further, the driving shaft RA' includes another (e.g., an opposite) end coupled to the second sub gear SG2'. As a result, the second sub gear SG2' rotates in the same direction as the rotation direction of the driving shaft RA'.

The second rotational moving unit RM2 is coupled to the first rotational moving unit RM1. As a result, the second rotational moving unit RM2 rotates in a direction opposite to the rotation direction of the first rotational moving unit RM1. The second rotational moving unit RM2 includes a third sub gear SG3 and a second support F2'.

The third sub gear SG3 is coupled to the second sub gear SG2'. As a result, the third sub gear SG3 rotates in a direction opposite to the rotation direction of the second sub gear SG2'. The second support F2' is fixed to the third sub gear SG3 and supports a second portion E12 of the flexible device 20. Double-sided tape may be disposed between the second support F2' and the second portion E12 to fix the second portion E12 to the second support F2', however, fixing means are not limited thereto.

Hereinafter, an operation for testing the flexible device 20 using the test apparatus 103 will be described with reference to FIGS. 7A and 7B.

Figure 7A:
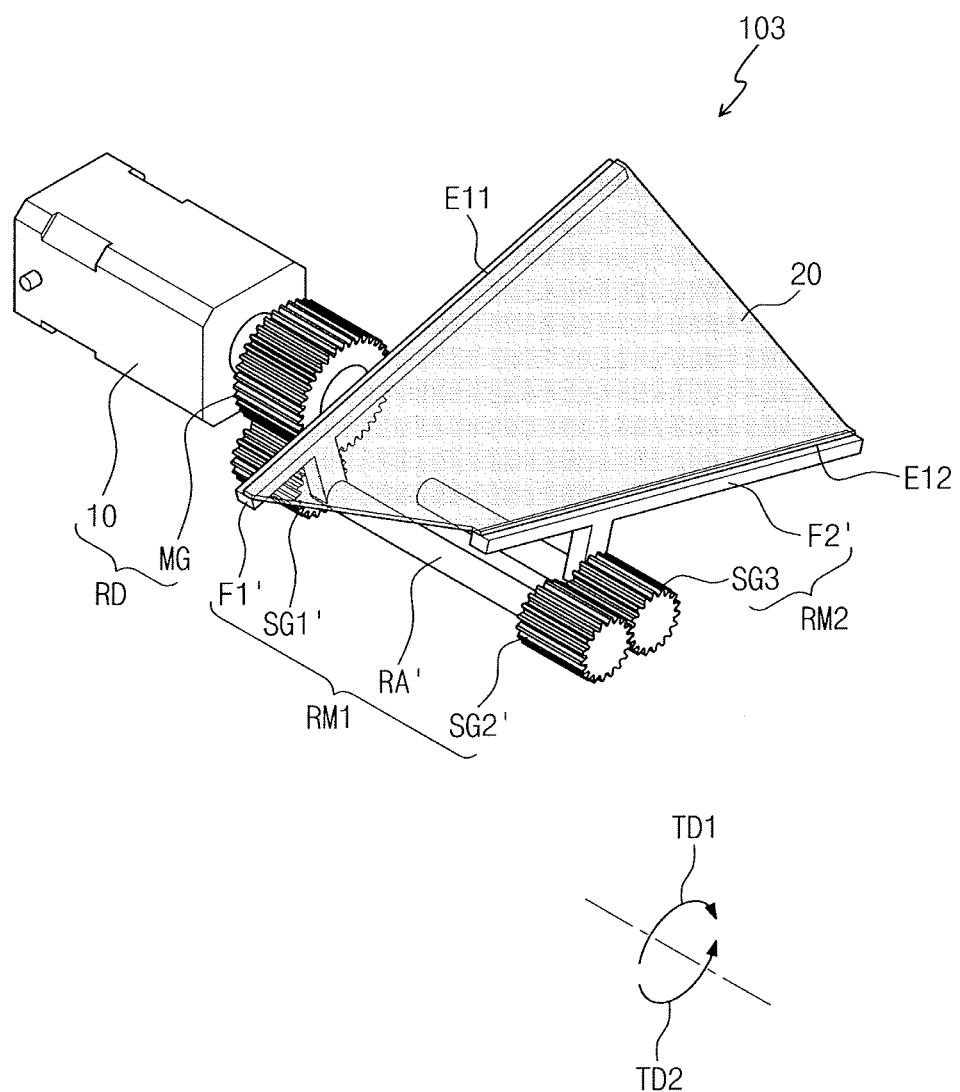
FIGS. 7A and 7B are views illustrating an operation for testing the flexible device using the test apparatus of FIG. 6, according to an exemplary embodiment of the present inventive concept.
Figure 7B:
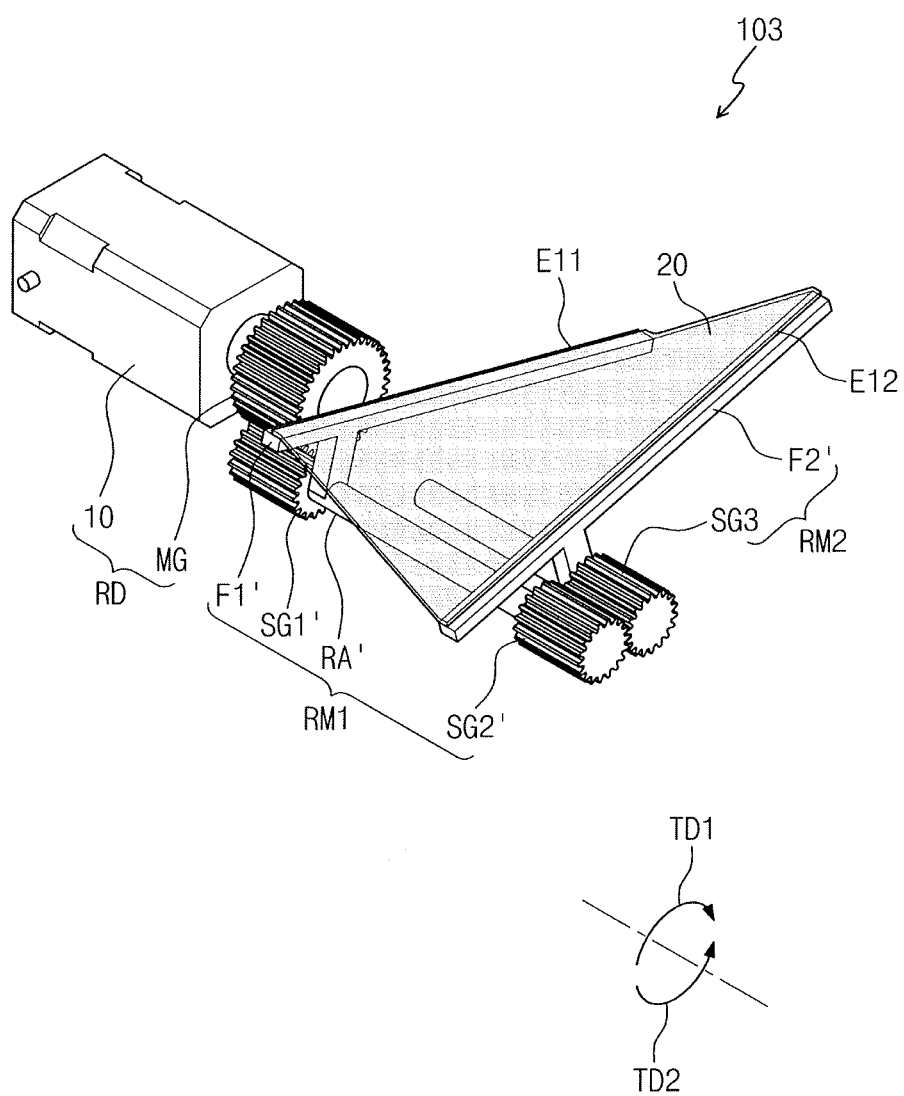

FIGS. 7A and 7B are views illustrating an operation for testing the flexible device using the test apparatus of FIG. 6, according to an exemplary embodiment of the present inventive concept.

Referring to FIG. 7A, the flexible device 20 is disposed above first and second rotational moving units RM1 and RM2. The first portion E11 of the flexible device 20 is fixed to the first support F1', and the second portion E12 of the flexible device 20 is fixed to the second support F2'.

The motor 10 is driven to allow the main gear MG coupled to the rotation shaft 15 of the motor 10 (see FIG. 1) to rotate in a first rotation direction TD1. The first sub gear SG1' coupled to the main gear MG rotates in a second rotation direction TD2. As a result, the first support F1' coupled to the first sub gear SG' rotates in the second rotation direction TD2.

The rotational force of the first sub gear SG1' is transferred to the second sub gear SG2' through the driving shaft RA'. As a result, the second sub gear SG2' rotates in the second rotation direction TD2. In this case, the third sub gear SG3 coupled to the second sub gear SG2' rotates in the first rotation direction TD1, and the second support F2' coupled to the third sub gear SG3 rotates in the first rotation direction TD1.

Thus, when the first support F1' rotates in the second rotation direction TD2 as a result of the rotational force generated by the rotational driving unit RD, and the second support F2' rotates in the first rotation direction TD1 that is opposite to the second rotation direction TD2, the flexible device 20 is twisted by the first and second supports F1' and F2', which rotate in different directions (e.g., opposite directions).

Referring to FIG. 7B, unlike the operation described with reference to FIG. 7A, when the motor 10 is driven in the second rotation direction TD2, the first support F1' rotates in the first rotation direction TD1, and the second support F2' rotates in the second rotation direction TD2. Thus, the flexible device 20 in FIG. 7B may be twisted in a direction opposite to that in which the flexible device 20 in FIG. 7A is twisted.

Each of the first and second supports F1' and F2' may rotate at an angle of about 0° to about 180°. However, exemplary embodiments of the preset inventive concept are not limited thereto. For example, the rotation angle of each of the first and second supports F1' and F2' may be variable according to a material or test purpose of the flexible device 20.

Various flexible properties such as, for example, the stretch rate, the roll rate, the fold rate, and the twist rate of a flexible device may be tested using the test apparatus according to the exemplary embodiments of the present inventive concept described herein.

Since each of the test apparatuses disclosed in the exemplary embodiments described herein includes the rotational driving unit that performs a test operation using the rotational force generated from the rotational driving unit, the rotational driving unit may be shared among test apparatuses according to the exemplary embodiments. Thus, to perform the various tests described herein, other components may be coupled to the rotational driving unit to realize the test apparatuses. For example, in exemplary embodiments, some components described herein may be removable, allowing for certain components to be interchanged.

While the present inventive concept has been particularly shown and described with reference to the exemplary embodiments thereof, it will be understood by those of ordinary skill in the art that various changes in form and detail may be made therein without departing from the spirit and scope of the present inventive concept as defined by the following claims.

What is claimed is:

1. A test apparatus for a flexible device, comprising:
   a rotational driving unit configured to generate a rotational force;
   a first support coupled to the rotational driving unit, wherein the first support is configured to rotate in response to the rotational force, and support a first portion of the flexible device; and
   a second support disposed adjacent to the first support, wherein the second support is configured to support a second portion of the flexible device.

2. The test apparatus of claim 1, wherein the rotational driving unit comprises:
   a motor comprising a rotation shaft; and
   a driving shaft coupled to the rotation shaft and the first support, wherein the driving shaft is configured to rotate together with the first support in response to the rotational force.

3. The test apparatus of claim 1, further comprising a support member configured to support the second support.

4. The test apparatus of claim 3, wherein the second support is fixed to the support member.

5. The test apparatus of claim 1, wherein the first support is configured to rotate using the driving shaft as a rotation shaft.

6. A test apparatus for a flexible device, comprising:
   a rotational driving unit configured to generate a rotational force;
   a first rotational moving unit configured to support a first portion of the flexible device, wherein the first rotational moving unit is coupled to the rotational driving unit and is configured to rotate in a second rotation direction in response to the rotational force; and
   a second rotational moving unit configured to support a second portion of the flexible device, and rotate in a first rotation direction opposite to the second rotation direction.

7. The test apparatus of claim 6, wherein the rotational driving unit comprises:
   a motor comprising a rotation shaft; and
   a main gear coupled to the rotation shaft, wherein the main gear and the rotation shaft are configured to rotate in the first rotation direction,
   wherein the first rotational moving unit comprises:
   a first sub gear coupled to the main gear and configured to rotate in the second rotation direction; and
   a first support coupled to the first sub gear and configured to rotate in the second rotation direction, wherein the first support is configured to support the first portion of the flexible device.

8. The test apparatus of claim 7, wherein the first rotational moving unit further comprises:

a driving shaft comprising a first end coupled to the first sub gear and configured to rotate in the second rotation direction; and a second sub gear coupled to a second end of the driving shaft and configured to rotate in the second rotation direction, wherein the second rotational moving unit comprises:

a third sub gear coupled to the second sub gear and configured to rotate in the first rotation direction; and a second support coupled to the third sub gear and configured to rotate in the first rotation direction, wherein the second support is configured to support the second portion of the flexible device.

9. A test apparatus for a flexible device, comprising:

a rotational driving unit configured to generate a rotational force; and a first linear moving unit coupled to the rotational driving unit and configured to convert the rotational force into a linear motion, wherein the first linear moving unit is coupled to a first portion of the flexible device.

10. The test apparatus of claim 9, wherein the rotational driving unit comprises:

a motor comprising a rotation shaft;

a driving shaft comprising a first end coupled to the rotation shaft and configured to rotate; and a gear coupled to a second end of the driving shaft and configured to rotate, wherein the first linear moving unit comprises:

a rack coupled to the gear and configured to linearly move as the gear rotates; and a support coupled to the rack and configured to support the first portion of the flexible device.

11. The test apparatus of claim 10, wherein the flexible device comprises a second portion, and the second portion is fixed to the driving shaft and wound around the driving shaft as the driving shaft rotates.

12. The test apparatus of claim 10, wherein the support and the driving shaft extend in a same direction, and the rack extends in a direction perpendicular to the same direction in which the support and the driving shaft extend.

13. The test apparatus of claim 12, wherein the first linear moving unit is configured to linearly move such that the support approaches the driving shaft as the driving shaft rotates.

14. The test apparatus of claim 9, further comprising a second linear moving unit configured to convert the rotational force into the linear motion, wherein the first and second linear moving units are configured to linearly move in opposite directions, and the second linear moving unit is coupled to a second portion of the flexible device.

15. The test apparatus of claim 14, wherein the rotational driving unit comprises:

a motor comprising a rotation shaft; and a main gear coupled to the rotation shaft, wherein the main gear and the rotation shaft are configured to rotate in a first rotation direction, wherein the first linear moving unit comprises:

a first sub gear coupled to the main gear and configured to rotate in a second rotation direction, opposite to the first rotation direction;

a first rack coupled to the first sub gear and configured to linearly move in a first direction as the first sub gear rotates; and a first support coupled to the first rack, wherein the second linear moving unit comprises:

a second sub gear coupled to the first sub gear and configured to rotate in the first rotation direction;

a second rack coupled to the second sub gear and configured to linearly move in a second direction, opposite to the first direction, as the second sub gear rotates; and a second support coupled to the second rack.

16. The test apparatus of claim 15, wherein the first support is configured to support the first portion of the flexible device, and the second support is configured to support a second portion of the flexible device.

17. The test apparatus of claim 16, wherein the first and second supports extend in a same direction, and the first and second racks extend in a direction perpendicular to the same direction in which the first and second supports extend.

18. A test apparatus for a flexible device, comprising:

a rotational driving unit configured to generate a rotational force, wherein the rotational driving unit comprises a motor comprising a rotation shaft, and a driving shaft coupled to the rotation shaft;

a first support coupled to the driving shaft, wherein the first support is configured to rotate in response to the rotational force, and support a first portion of the flexible device; and a second support disposed adjacent to the first support, wherein the second support is fixed to a support member, remains stationary in response to the rotational force, and is configured to support a second portion of the flexible device.

19. The test apparatus of claim 18, wherein the first and second supports are configured to have an angle of about 0° to about 270° therebetween upon rotating the first support.

20. The test apparatus of claim 18, wherein the first support is configured to rotate about an axis defined by the driving shaft.

* * * * *